US012605565B2

(12) United States Patent
Hytonen et al.

(10) Patent No.: US 12,605,565 B2
(45) Date of Patent: Apr. 21, 2026

(54) DELIVERY MACHINE LIMITATION GUIDED RADIATION THERAPY TREATMENT PLANNING

(71) Applicant: Siemens Healthineers International AG, Steinhausen (CH)

(72) Inventors: Roni Hytonen, Espoo (FI); Jari Lindberg, Helsinki (FI); Perttu Niemela, Espoo (FI); Francisco Roberto Cassetta Junior, Dietikon (CH); Reynald Vanderstraeten, Ukkel (BE)

(73) Assignee: SIEMENS HEALTHINEERS INTERNATIONAL AG, Steinhausen (CH)

( * ) Notice: Subject to any disclaimer, the term of this patent is extended or adjusted under 35 U.S.C. 154(b) by 243 days.

(21) Appl. No.: 18/482,357

(22) Filed: Oct. 6, 2023

(65) Prior Publication Data

US 2025/0114639 A1 Apr. 10, 2025

(51) Int. Cl.
*A61N 5/10* (2006.01)
*G16H 20/40* (2018.01)
*G16H 40/40* (2018.01)

(52) U.S. Cl.
CPC ......... *A61N 5/1031* (2013.01); *A61N 5/1048* (2013.01); *G16H 20/40* (2018.01); *G16H 40/40* (2018.01); *A61N 2005/1087* (2013.01)

(58) Field of Classification Search
CPC ................ A61N 5/1031; A61N 5/1048; A61N 2005/1087; G16H 20/40; G16H 40/40
See application file for complete search history.

(56) References Cited

U.S. PATENT DOCUMENTS

| | | | |
|---|---|---|---|
| 11,278,737 | B2 | 3/2022 | Peltola et al. |
| 2020/0105395 | A1 | 4/2020 | Huth et al. |
| 2020/0129782 | A1 | 4/2020 | Stål et al. |

(Continued)

OTHER PUBLICATIONS

Gao et al. Technical Note: Plan-delivery-time constrained inverse optimization method with minimum-MU-per-energy-layer (MMPEL) for efficient pencil beam scanning proton therapy. Med Phys. Sep. 2020;47(9):3892-3897. doi: 10.1002/mp.14363. (Year: 2020).*

(Continued)

*Primary Examiner* — Eliza A Lam
(74) *Attorney, Agent, or Firm* — Harness, Dickey & Pierce, P.L.C.

(57) ABSTRACT

A system for planning a radiation therapy treatment to be performed by a radiation therapy machine includes at least one processor and a memory storing computer executable instructions. The at least one processor is configured to execute the computer executable instructions to cause the system to generate a radiation therapy treatment plan prescribing a plurality of energy layers associated with a plurality of spots in a treatment target. The radiation therapy treatment plan is based on a plurality of minimum monitor unit values, each of which is for a respective energy layer among the plurality of energy layers. Each of the plurality of minimum monitor unit values is based on machine parameters for the radiation therapy machine and/or based on a minimum monitor unit objective function for the radiation therapy machine.

18 Claims, 9 Drawing Sheets

(56)     References Cited

U.S. PATENT DOCUMENTS

2021/0038914  A1*   2/2021  Traneus ............... A61N 5/1031
2021/0308485  A1*  10/2021  Koponen ............. A61N 5/1043
2022/0176156  A1     6/2022  Meijers et al.

OTHER PUBLICATIONS

Wenhua, C. et al., "Incorporating deliverable monitor unit constraints into spot intensity optimization in intensity modulated proton therapy treatment planning," Phys Med Biol., pp. 5113-5125, Aug. 7, 2013.
Gao, H. et al., "Technical Note: Plan-delivery-time constrained inverse optimization method with minimum-MU-per-energy-layer (MMPEL) for efficient pencil beam scanning proton therapy," Med. Phy. 47, pp. 3892-3897, Sep. 2020.

* cited by examiner

TARGET 218

CONTOUR

BEAM 220

BEAMLET 214    216

302
PATIENT
INFORMATION

304
PLAN
DEVELOPMENT/
EVALUATION/
OPTIMIZATION

308
TREATMENT

306

300

DETERMINE A MINIMUM MONITOR UNIT FOR EACH ENERGY LAYER PRESCRIBED BY A RADIATION THERAPY TREATMENT PLAN BASED ON MACHINE PARAMETERS FOR A RADIATION THERAPY MACHINE
S604

GENERATE A DELIVERABLE RADIATION THERAPY TREATMENT PLAN BY PERFORMING AN OPTIMIZATION BASED ON THE MINIMUM MONITOR UNIT FOR EACH ENERGY LAYER
S606

TREATMENT
S608

S604

COMPUTE A MINIMUM DELIVERABLE MONITOR UNIT AND A MONITOR UNIT RATE SATURATION POINT FOR AN ENERGY LAYER BASED ON THE MACHINE PARAMETERS FOR THE RADIATION THERAPY MACHINE
S704

DETERMINE A MINIMUM MONITOR UNIT FOR THE ENERGY LAYER BASED ON THE MINIMUM DELIVERABLE MONITOR UNIT AND THE MONITOR UNIT RATE SATURATION POINT
S706

S606

PERFORM OPTIMIZATION PROCESS
S804

REMOVE SPOTS AT ENERGY LAYER HAVING MONITOR
UNIT BELOW THE MINIMUM MONITOR UNIT FOR THE
ENERGY LAYER
S806

DERIVE MINIMUM MONITOR UNIT OBJECTIVE FUNCTION BASED ON MACHINE PARAMETERS FOR A RADIATION THERAPY MACHINE
S904

GENERATE A DELIVERABLE RADIATION THERAPY TREATMENT PLAN BY PERFORMING AN OPTIMIZATION BASED ON MINIMUM MONITOR UNIT OBJECTIVE FUNCTION
S906

TREATMENT
S908

DELIVERY MACHINE LIMITATION GUIDED RADIATION THERAPY TREATMENT PLANNING

TECHNICAL FIELD

One or more example embodiments relate to radiation therapy treatment planning and radiation therapy treatment.

BACKGROUND

Radiation therapy involves directing a beam of high energy proton, photon, ion, or electron radiation into a target volume in a treatment target of unhealthy tissue (e.g., a tumor or lesion).

Before performing radiation therapy on a patient, a treatment plan specific to that patient is developed. The treatment plan defines various aspects of the radiation therapy using simulations and optimizations that may be based on past experiences. In general, the purpose of the treatment plan is to deliver sufficient radiation to unhealthy tissue while minimizing exposure of surrounding healthy tissue to that radiation.

SUMMARY

The scope of protection sought for various example embodiments is set out by the independent claims. The example embodiments and/or features, if any, described in this specification that do not fall under the scope of the independent claims are to be interpreted as examples useful for understanding various embodiments.

Independent of the grammatical term usage, individuals with male, female or other gender identities are included within the term.

At least one example embodiment provides a system for planning a radiation therapy treatment to be performed by a radiation therapy machine. The system includes at least one processor and a memory storing computer executable instructions. The at least one processor is configured to execute the computer executable instructions to cause the system to generate a radiation therapy treatment plan prescribing a plurality of energy layers associated with a plurality of spots in a treatment target, the radiation therapy treatment plan being based on a plurality of minimum monitor unit values, each of the plurality of minimum monitor unit values being for a respective energy layer among the plurality of energy layers, and each of the plurality of minimum monitor unit values being based on machine parameters for the radiation therapy machine.

At least one other example embodiment provides a radiation therapy treatment system including: a system for planning a radiation therapy treatment; and a radiation therapy machine configured to provide radiation therapy treatment according to a radiation therapy treatment plan. The system for planning the radiation therapy treatment includes at least one processor and a memory storing computer executable instructions. The at least one processor is configured to execute the computer executable instructions to cause the system to generate the radiation therapy treatment plan prescribing a plurality of energy layers associated with a plurality of spots in a treatment target, the radiation therapy treatment plan being based on a plurality of minimum monitor unit values, each of the plurality of minimum monitor unit values being for a respective energy layer among the plurality of energy layers, and each of the plurality of minimum monitor unit values being based on machine parameters for the radiation therapy machine.

At least one other example embodiment provides a system for planning a radiation therapy treatment to be performed by a radiation therapy machine. The system includes means for generating a radiation therapy treatment plan prescribing a plurality of energy layers associated with a plurality of spots in a treatment target, the radiation therapy treatment plan being based on a plurality of minimum monitor unit values, each of the plurality of minimum monitor unit values being for a respective energy layer among the plurality of energy layers, and each of the plurality of minimum monitor unit values being based on machine parameters for the radiation therapy machine.

At least one other example embodiment provides a method for planning a radiation therapy treatment to be performed by a radiation therapy machine, the method comprising: generating a radiation therapy treatment plan prescribing a plurality of energy layers associated with a plurality of spots in a treatment target, the radiation therapy treatment plan being based on a plurality of minimum monitor unit values, each of the plurality of minimum monitor unit values being for a respective energy layer among the plurality of energy layers, and each of the plurality of minimum monitor unit values being based on machine parameters for the radiation therapy machine.

At least one other example embodiment provides a non-transitory computer-readable medium storing computer executable instructions that, when executed by at least one processor, cause the at least one processor to perform a method for planning a radiation therapy treatment to be performed by a radiation therapy machine, the method comprising: generating a radiation therapy treatment plan prescribing a plurality of energy layers associated with a plurality of spots in a treatment target, the radiation therapy treatment plan being based on a plurality of minimum monitor unit values, each of the plurality of minimum monitor unit values being for a respective energy layer among the plurality of energy layers, and each of the plurality of minimum monitor unit values being based on machine parameters for the radiation therapy machine.

According to one or more example embodiments, the machine parameters may include at least one of a monitor unit rate range for the radiation therapy machine, a minimum spot duration for the radiation therapy machine, or transmission parameters for the radiation therapy machine.

The at least one processor may be configured to execute the computer executable instructions to cause the system to: compute a minimum deliverable monitor unit value for a first energy layer, among the plurality of energy layers, based on the machine parameters for the radiation therapy machine; compute a monitor unit rate saturation point for the first energy layer based on the machine parameters for the radiation therapy machine; and determine a minimum monitor unit value for the first energy layer based on the minimum deliverable monitor unit value and the monitor unit rate saturation point for the first energy layer.

The at least one processor may be configured to execute the computer executable instructions to cause the system to determine the plurality of minimum monitor unit values based on a minimum monitor unit saturation curve for the radiation therapy machine, the minimum monitor unit saturation curve derived based on the machine parameters for the radiation therapy machine.

The minimum monitor unit saturation curve may be indicative of a minimum deliverable monitor unit value and a monitor unit rate saturation point for each of the plurality of energy layers.

The minimum deliverable monitor unit value and the monitor unit rate saturation point for each of the plurality of energy layers may be based on the machine parameters for the radiation therapy machine.

At least one example embodiment provides a system for planning a radiation therapy treatment to be performed by a radiation therapy machine. The system includes at least one processor and a memory storing computer executable instructions. The at least one processor is configured to execute the computer executable instructions to cause the system to generate a radiation therapy treatment plan prescribing a plurality of energy layers associated with a plurality of spots in a treatment target, the radiation therapy treatment plan having a plurality of minimum monitor unit values, the plurality of minimum monitor unit values generated based on a minimum monitor unit objective function for the radiation therapy machine.

At least one other example embodiment provides a radiation therapy treatment system, including: a system for planning a radiation therapy treatment; and a radiation therapy machine configured to provide radiation therapy treatment according to the radiation therapy treatment plan. The system for planning the radiation therapy treatment includes at least one processor and a memory storing computer executable instructions. The at least one processor is configured to execute the computer executable instructions to cause the system to generate a radiation therapy treatment plan prescribing a plurality of energy layers associated with a plurality of spots in a treatment target, the radiation therapy treatment plan having a plurality of minimum monitor unit values, the plurality of minimum monitor unit values generated based on a minimum monitor unit objective function for the radiation therapy machine.

At least one example embodiment provides a system for planning a radiation therapy treatment to be performed by a radiation therapy machine. The system includes means for generating a radiation therapy treatment plan prescribing a plurality of energy layers associated with a plurality of spots in a treatment target, the radiation therapy treatment plan having a plurality of minimum monitor unit values, the plurality of minimum monitor unit values generated based on a minimum monitor unit objective function for the radiation therapy machine.

At least one example embodiment provides a method for planning a radiation therapy treatment to be performed by a radiation therapy machine, the method comprising: generating a radiation therapy treatment plan prescribing a plurality of energy layers associated with a plurality of spots in a treatment target, the radiation therapy treatment plan having a plurality of minimum monitor unit values, the plurality of minimum monitor unit values generated based on a minimum monitor unit objective function for the radiation therapy machine.

At least one example embodiment provides a non-transitory computer-readable medium storing computer executable instructions that, when executed by at least one processor, cause the at least one processor to perform a method for planning a radiation therapy treatment to be performed by a radiation therapy machine, the method comprising: generating a radiation therapy treatment plan prescribing a plurality of energy layers associated with a plurality of spots in a treatment target, the radiation therapy treatment plan having a plurality of minimum monitor unit values, the plurality of minimum monitor unit values generated based on a minimum monitor unit objective function for the radiation therapy machine.

According to one or more example embodiments, the at least one processor may be configured to execute the computer executable instructions to cause the system to derive the minimum monitor unit objective function based on machine parameters for the radiation therapy machine.

Each of the plurality of minimum monitor unit values may be associated with a respective energy layer among the plurality of energy layers.

The at least one processor may be configured to execute the computer executable instructions to cause the system to generate the radiation therapy treatment plan according to at least the minimum monitor unit objective function, a dosimetric objective function and a weight factor.

The minimum monitor unit objective function may be a sum of energy layer and spot-wise cost functions that are piecewise linear.

At least one example embodiment provides a system for planning a radiation therapy treatment to be performed by a radiation therapy machine. The system includes at least one processor and a memory storing computer executable instructions. The at least one processor is configured to execute the computer executable instructions to cause the system to generate a radiation therapy treatment plan for a treatment target based on a minimum monitor unit value computed for each of a plurality of energy layers prescribed by the radiation therapy treatment plan, each minimum monitor unit value based on machine parameters for the radiation therapy machine.

At least one other example embodiment provides a system for radiation therapy treatment, comprising: a system for planning a radiation therapy treatment; and a radiation therapy machine configured to apply radiation therapy treatment according to the radiation therapy treatment plan. The system for planning the radiation therapy treatment includes at least one processor and a memory storing computer executable instructions. The at least one processor is configured to execute the computer executable instructions to cause the system to generate a radiation therapy treatment plan for a treatment target based on a minimum monitor unit value computed for each of a plurality of energy layers prescribed by the radiation therapy treatment plan, each minimum monitor unit value based on machine parameters for the radiation therapy machine.

At least one other example embodiment provides a system for planning a radiation therapy treatment to be performed by a radiation therapy machine. The system includes means for generating a radiation therapy treatment plan for a treatment target based on a minimum monitor unit value computed for each of a plurality of energy layers prescribed by the radiation therapy treatment plan, each minimum monitor unit value based on machine parameters for the radiation therapy machine.

At least one other example embodiment provides a method for planning a radiation therapy treatment to be performed by a radiation therapy machine, the method comprising: generating a radiation therapy treatment plan for a treatment target based on a minimum monitor unit value computed for each of a plurality of energy layers prescribed by the radiation therapy treatment plan, each minimum monitor unit value based on machine parameters for the radiation therapy machine.

At least one other example embodiment provides a non-transitory computer-readable medium storing computer executable instructions that, when executed by at least one processor, cause the at least one processor to perform a method for planning a radiation therapy treatment to be performed by a radiation therapy machine, the method comprising: generating a radiation therapy treatment plan for a treatment target based on a minimum monitor unit value computed for each of a plurality of energy layers prescribed by the radiation therapy treatment plan, each minimum monitor unit value based on machine parameters for the radiation therapy machine According to one or more example embodiments, the at least one processor may be configured to execute the computer executable instructions to cause the system to generate the radiation therapy treatment plan by performing an optimization based on the minimum monitor unit value for each of the plurality of energy layers.

The machine parameters may include at least one of a monitor unit rate range for the radiation therapy machine, a minimum spot duration for the radiation therapy machine, or transmission parameters for the radiation therapy machine.

The at least one processor may be configured to execute the computer executable instructions to cause the system to: compute a minimum deliverable monitor unit value for a first energy layer, among the plurality of energy layers, based on the machine parameters for the radiation therapy machine; compute a monitor unit rate saturation point for the first energy layer based on the machine parameters for the radiation therapy machine; and determine a minimum monitor unit value for the first energy layer based on the minimum deliverable monitor unit value and the monitor unit rate saturation point for the first energy layer.

The at least one processor may be configured to execute the computer executable instructions to cause the system to compute the minimum monitor unit value for each of the plurality of energy layers based on a minimum monitor unit saturation curve for the radiation therapy machine, the minimum monitor unit saturation curve derived based on the machine parameters for the radiation therapy machine.

BRIEF DESCRIPTION OF THE DRAWINGS

Example embodiments will become more fully understood from the detailed description given herein below and the accompanying drawings, wherein like elements are represented by like reference numerals, which are given by way of illustration only and thus are not limiting of this disclosure.

Figure 1:
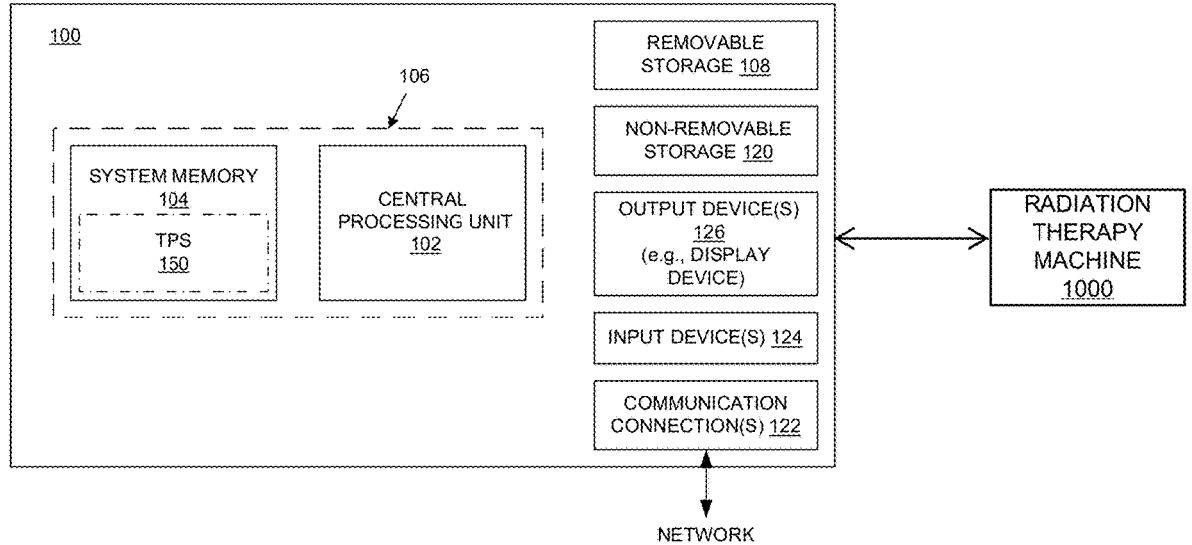
FIG. 1 is a block diagram of an example of a system upon which one or more example embodiments may be implemented.

It should be noted that these figures are intended to illustrate the general characteristics of methods, structure and/or materials utilized in certain example embodiments and to supplement the written description provided below. These drawings are not, however, to scale and may not precisely reflect the precise structural or performance characteristics of any given embodiment and should not be interpreted as defining or limiting the range of values or properties encompassed by example embodiments. The use of similar or identical reference numbers in the various drawings is intended to indicate the presence of a similar or identical element or feature.

DETAILED DESCRIPTION

Various example embodiments will now be described more fully with reference to the accompanying drawings in which some example embodiments are shown.

Detailed illustrative embodiments are disclosed herein. However, specific structural and functional details disclosed herein are merely representative for the purposes of describing example embodiments. The example embodiments may, however, be embodied in many alternate forms and should not be construed as limited to only the embodiments set forth herein.

It should be understood that there is no intent to limit example embodiments to the particular forms disclosed. On the contrary, example embodiments are to cover all modifications, equivalents, and alternatives falling within the scope of this disclosure. Like numbers refer to like elements throughout the description of the figures.

As discussed herein the terminology "one or more" and "at least one" may be used interchangeably.

As discussed herein, a radiation therapy treatment plan may also be referred to as a radiation treatment plan, a treatment plan or a plan. Moreover, the terms "proposed" and "candidate" may be used interchangeably in the context of a radiation therapy treatment plan.

It will be appreciated that a number of example embodiments may be used in combination.

Unless specifically stated otherwise as apparent from the following discussion, it is appreciated that throughout the present disclosure, discussions utilizing terms such as "accessing," "determining," "storing," "assigning," "adjusting," "combining," "summing," "adding," "optimizing," "minimizing," "producing," "generating," "identifying," "setting," "increasing," "evaluating," "calculating," or the like, may refer to actions and processes of a computer system or similar electronic computing device or processor. The computer system or similar electronic computing device manipulates and transforms data represented as physical (electronic) quantities within the computer system memories, registers or other such information storage, transmission or display devices.

The discussion to follow may include terms such as "weight," "metric," "intensity," "monitor unit," etc. Unless otherwise noted, a value is associated with each such term. For example, a weight (e.g., a weight of a spot or beamlet) has a value, and a metric has a value. For simplicity, the term "weight" or "metric" or "intensity" or "monitor unit" may refer to a value of the weight or metric or intensity or monitor unit itself, unless otherwise noted or apparent from the discussion.

Although example embodiments may be discussed herein with regard to intensity modulated particle therapy (IMPT) (spot or pencil beam scanning), example embodiments should not be limited to this example. Rather, example embodiments may also be applicable to IMRT.

FIG. 1 is a block diagram of an example of a system upon which one or more example embodiments may be implemented. The system includes a computer system 100 and a radiation therapy machine 1000 in two-way communication with one another.

The radiation therapy machine 1000 may be a treatment modality for providing radiation therapy treatment, such as intensity modulated radiation therapy (IMRT) or intensity modulated particle therapy (IMPT). These radiation therapy treatments will be discussed in more detail later.

The computer system 100 includes at least one central processing unit (or other processing circuitry) 102, memory 104, removable storage 108, non-removable storage 120, and communications connection(s) 122, to enable the system to communicate with other devices (e.g., in a networked environment using logical connections to one or more remote computers).

The system 100 further includes one or more input devices 124 (e.g., a keyboard, mouse, pen, voice input device, touch screen or other input device, etc.) and one or more output devices 126, such as a display device, speakers, printer, etc. A display device may be, for example, a cathode ray tube display, a light-emitting diode display, a liquid crystal display, a touch screen display, a combination thereof, or the like.

In FIG. 1, the memory 104 includes computer-readable instructions, data structures, program modules, and/or the like, associated with a treatment planning system (TPS) 150, which may also be referred to as an optimizer. However, the TPS 150 may instead reside in any one of the computer storage media used by the system 100, may be distributed over some combination of the computer storage media, may be distributed over some combination of networked computers, or may be present in the cloud. As discussed later, the TPS 150 is configured to generate, optimize and evaluate radiation treatment plans (e.g., candidate or proposed treatment plans) and produce a final (optimized and deliverable) treatment plan. The final treatment plan may be utilized to apply, via the radiation therapy machine 1000, radiation therapy treatment to a treatment target of a patient.

With regard to treatment modalities, in IMRT, a photon beam includes a number of beam segments or beamlets prescribed by the treatment plan. The beam is shaped using multi-leaf collimators (MLCs) either before or while the beam is directed into the treatment target. In one or more such embodiments, a maximum energy (e.g., 80 MeV) for the beam is specified, and an energy for each of the beamlets is determined as a percentage (100% or less) or equivalent fraction of the maximum beam energy. Thus, each of the beamlets can be weighted based on its energy layer. By weighting based on the energy per beamlet, each beamlet is in effect also weighted based on its intensity. The weight of each beamlet may be expressed as a monitor unit (MU).

In IMPT (e.g., spot or pencil beam scanning), a proton or ion beam is directed to spots in a treatment target as prescribed by the treatment plan. The prescribed spot locations are typically arranged in a fixed (raster) pattern for each energy layer of the beam, and the beam is delivered on a fixed scanning path within an energy layer. Each spot can be weighted based on, for example, the number of protons received at the spot when irradiated by the beam. The weight of each spot may be expressed as a value of a monitor unit (e.g., number of protons) or MU.

A radiation therapy treatment plan (e.g., optimized, deliverable and/or candidate) includes values of parameters that can affect dose and/or dose rate, as well as other parameters. Depending on the treatment modality, the parameters may include, but are not limited to: beam shape (collimation); number and arrangement of spots for spot (pencil beam) scanning, and spot weights; beamlet weights; beamlet intensities or energies; beam/beamlet directions; prescribed dose and prescribed dose rate; a number of irradiations of a target volume; a duration of each of the irradiations (irradiation times); and a dose deposited in each of the irradiations. The parameters may also include a period of time during which the irradiations are applied (e.g., a number of irradiations are applied over a period of time such as an hour, with each irradiation in the period of time separated from the next by another period of time) and an interval of time between each period of irradiations (e.g., each hour-long period is separated from the next by a day).

The relatively large number of parameters and their ranges of values can lead to an effectively infinite number of potential treatment plans, and therefore consistently and efficiently generating and evaluating high-quality treatment plans is well beyond the capability of the human mind and relies on the use of a computing system.

To deliver the prescribed dose/dose rate of radiation, the radiation treatment plan may be converted (e.g., by the TPS 150) into radiation therapy application parameters for a radiation therapy machine (e.g., radiation therapy machine 1000). Radiation therapy application parameters may include, for example, beam currents of a proton, ion, or photon beam, the number of protons, ions, or photons per time segment to be emitted by the accelerator, magnet currents, settings to achieve the prescribed energy of protons, ions, or photons at the target volume, and/or the measurement range of a dose monitor system.

During treatment, a beam enters a nozzle of the radiation therapy machine 1000, which may include one or more components that affect (e.g., decrease, modulate, etc.) the energy of the beam, to control the dose/dose rate delivered by the beam and/or to control the dose versus depth curve of the beam, depending on the type of beam. For example, for a proton beam or an ion beam that has a Bragg peak, the nozzle can control the location of the Bragg peak in the treatment target laterally to the beam axis. In other examples, energy modulation is performed outside of the nozzle (e.g., upstream of the nozzle).

The nozzle is mounted on a moveable gantry so that the beam may be delivered from different directions (angles) relative to a patient (treatment target) on the patient support device, and the position of the patient support device relative to the beam may also be changed.

Figure 2A:
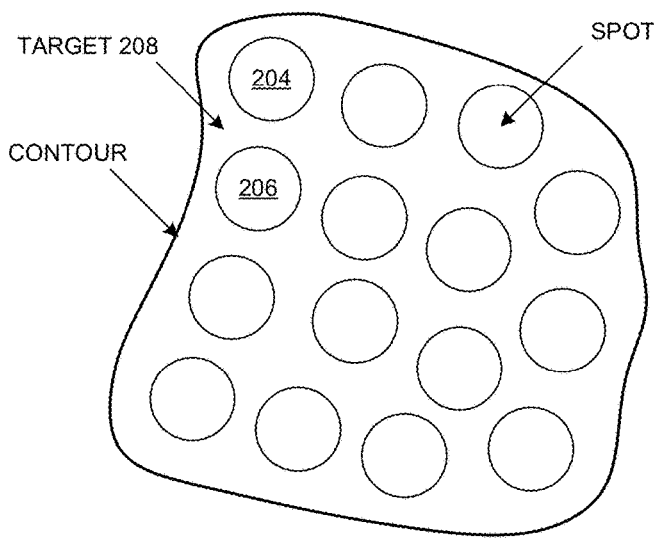
FIGS. 2A and 2B illustrate examples of a beam's eye view of a treatment target according to example embodiments.

FIG. 2A illustrates an example of a beam's eye view of a treatment target 208 in some (e.g., IMPT) example embodiments. The treatment target 208 may coincide with the shape of the volume being treated (e.g., the contour of the treatment target may coincide with the contour of a tumor), the treatment target may be larger than the volume being treated, or the treatment target may correspond to a portion (e.g., a sub-volume) of the volume being treated.

In these example embodiments, an arrangement of spots (e.g., the spots 204 and 206) is mapped onto the treatment target 208. Each spot corresponds to a particular location in the treatment target 208. The spots in the treatment target 208 may be irradiated with a raster scan (two-dimensional emission) of a spot scanning beam (pencil beam). Generally speaking, a first pencil beam is aimed at the first spot 204 in the treatment target 208, a dose rate is delivered to that spot, then a second pencil beam is aimed at the second spot 206 in the treatment target, a dose rate is delivered to the second spot 206, and so on. Spots with a weight or MU below a minimum MU (e.g., spots having a weight or MU of zero) are not irradiated.

Each spot scanning beam can deliver a relatively high dose rate (a relatively high dose in a relatively short period of time) to each spot. For example, if necessary, the spot scanning beam can deliver above 40 grays (Gy) to each spot in less than one second.

Figure 2B:
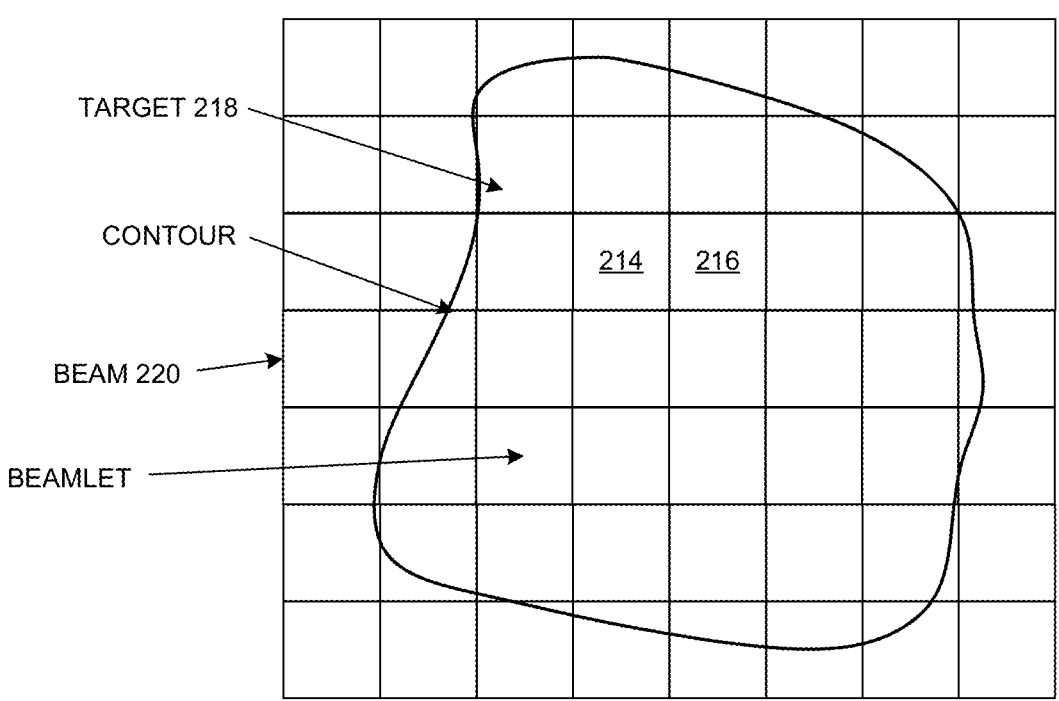

FIG. 2B illustrates an example of a beam's eye view of a treatment target 208 in other (e.g., IMRT) example embodiments. In these example embodiments, the beam 220 that is used to irradiate the treatment target 208 includes an array of beamlets (e.g., the beamlets 214 and 216) that is mapped onto the treatment target 208. Each beamlet corresponds to a particular location in the treatment target 208. A maximum energy for the beam 220 is specified, and an energy for each of the beamlets 214, 216, etc., is determined as a percentage or fraction of the maximum beam energy.

As with spot scanning, each beamlet is capable of delivering a relatively high dose rate (a relatively high dose in a relatively short period of time). For example, if necessary, each beamlet can deliver above 40 grays (Gy) in less than one second. Beamlets with a weight or MU below a minimum MU (e.g., beamlets having a weight or MU of zero) are not used during treatment.

Figure 3:
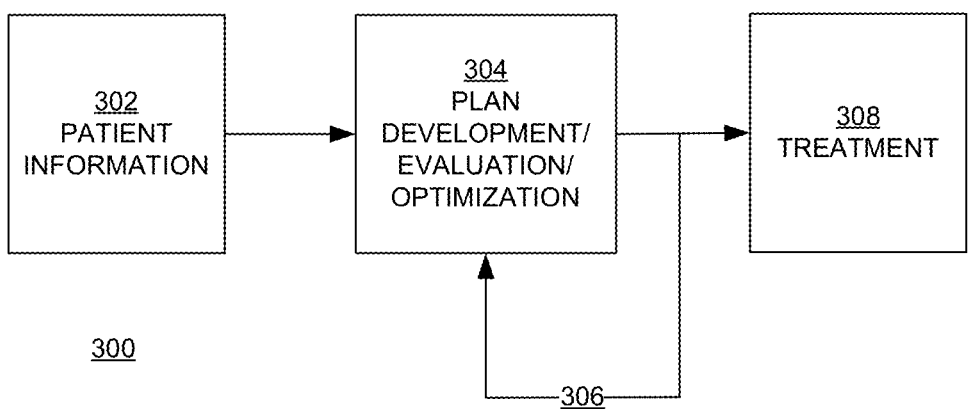
FIGS. 3 and 4 are block diagrams illustrating an example of an automated radiation therapy treatment planning process according to example embodiments.

FIG. 3 is a block diagram illustrating an example of an automated radiation therapy treatment planning and treatment process 300, according to example embodiments. The process 300, in whole or in part, may be implemented as or in conjunction with a software program, hardware logic, or a combination thereof on/using the computer system 100 and the radiation therapy machine 1000 in FIG. 1.

Referring to FIG. 3, in step 302 the computer system 100 obtains three-dimensional (3D) images of a patient, and segments and contours organs and other structures in the patient (the patient geometry). In steps 304 and 306, as will be discussed in more detail below with regard to FIG. 4, the system 100 develops and evaluates a radiation therapy treatment plan based on the information obtained in step 302, and other information.

In step 308, if the treatment plan developed by the system 100 is satisfactory (e.g., satisfies prescribed clinical goals), then the radiation therapy treatment plan may be used for treatment of the patient (e.g., using the radiation therapy machine 1000). If not, then the system 100 may iteratively modify aspects of the treatment plan and/or of the clinical goals until a satisfactory plan is generated, and then the satisfactory radiation therapy treatment plan may be utilized for treatment of the patient (e.g., using the radiation therapy machine 1000). The clinical goals may be expressed in terms of, for example, a set of quality metrics, such as target homogeneity, conformity to the treatment target, critical organ sparing, and the like, with respective target values for the quality metrics.

Figure 4:
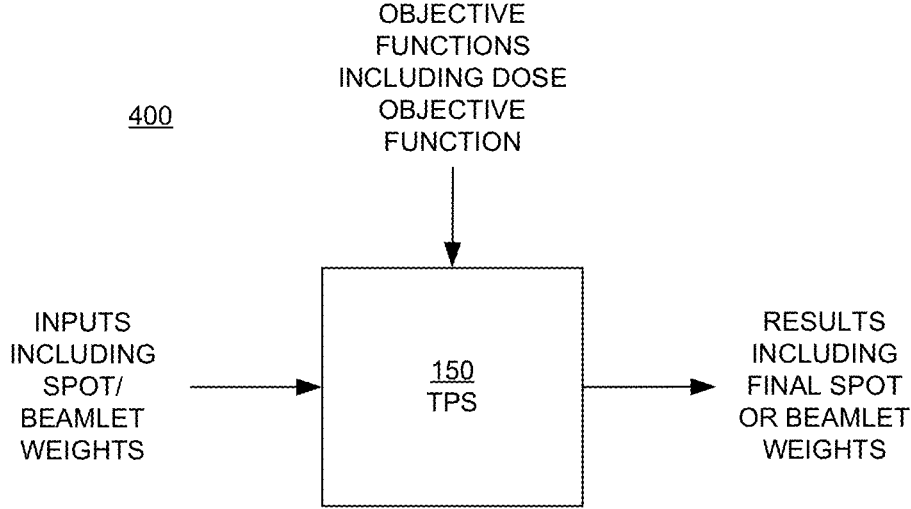

FIG. 4 is a block diagram illustrating an example of an automated radiation therapy treatment planning process 400, according to example embodiments. The process 400, in whole or in part, may be implemented as a software program, hardware logic, or a combination thereof on/using the system 100 of FIG. 1. For example, the process 400 may be performed at the TPS 150. The process 400 corresponds generally to steps 304 and 306 in FIG. 3.

Referring to FIG. 4, the TPS 150 accesses or receives (e.g., from the memory 104 of FIG. 1) information that includes input parameters such as those mentioned above. The TPS 150 may also access or receive information specific to the patient to be treated (e.g., the above-discussed patient geometry), including information that describes a treatment target (region of interest (ROI)), which may include a planned target volume (PTV), gross tumor volume (GTV), clinical target volume (CTV), and/or organs-at-risk (OARs).

The TPS 150 also accesses or receives objective functions defined for the treatment of the patient. Objective functions are mathematical formulations of variables (parameters such as those mentioned above) that may have an effect on achieving specified clinical goals. The objective functions are used to evaluate proposed radiation therapy treatment plans to determine whether or not the clinical goals that are specified for treatment of a patient are satisfied.

An example of a dose objective function f(d) is: $f(d)=\Sigma$ $(w_i)(d_i-d_p)^2$, where $w_i$ is a weight per voxel in a treatment target, $d_i$ is the dose per voxel projected to be received according to a proposed treatment plan, $d_p$ is the prescribed dose per voxel, and the summation 2 is over all voxels i in the treatment target. A voxel may be a spot in the treatment target irradiated by a spot scanning beam, or may correspond to a location in the treatment target into which a beamlet is directed. In this example, the goal is to minimize the value of the dose objective function (in this example, the dose across the treatment target becomes more uniform as the value of the function decreases). In practice, there may be several objective functions (in addition to the dose objective function) that are to be minimized in order to achieve a final (e.g., an optimal final) treatment plan. Some other objective functions, according to example embodiments, will be discussed in more detail later. The objective functions may conflict with each other; that is, minimizing one objective function may penalize another objective function, and so minimizing all of the objective functions may not be achievable. Thus, in example embodiments, the objective functions may be weighted and summed to provide a total of all of the objective functions ($F_{Tot}$), and that total may then be minimized.

Still referring to FIG. 4, for IMPT, for example, the information accessed or received by the TPS 150 may include, but is not limited to, the number and positions (pattern or arrangement) of spots, a value (e.g., an initial value) of a weight for each spot in the treatment target, and a dosimetric objective function that accounts for the dose objective for the PTV and OARs. The weight of each spot may be expressed as a value of a MU corresponding to, for example, the number of particles (e.g., protons or ions) per spot. As noted above with regard to FIG. 2A, each spot corresponds to a location in the treatment target. As such, each spot weight can be referred to as a "locational" weight or location-based weight: a spot corresponds to a location, a weight corresponds to the spot, and thus the spot weight corresponds to the location. In essence, according to example embodiments, a spot weight is assigned to or associated with a respective location inside the treatment target.

In another example, for IMRT, the information accessed or received by the TPS 150 may include, but is not limited to, the number of beamlets, a value (e.g., an initial value) of a weight for each beamlet (where the weight corresponds to a fraction or percentage of the beam energy), and a dosimetric objective function that accounts for the dose objective for the PTV and OARs. The weight of each beamlet may also be expressed as a value of a MU corresponding to, for example, the beamlet's intensity or energy as a fraction or percentage of beam intensity or energy. As noted above with regard to FIG. 2B, each beamlet corresponds to a location in the treatment target. Similar to that of a spot weight, each beamlet weight can be referred to as a locational weight or location-based weight: a beamlet corresponds to a location, a weight corresponds to the beamlet, and thus the beamlet weight corresponds to the location. In essence, according to these example embodiments, a beamlet weight is assigned to or associated with a respective location inside the treatment target.

When generating and optimizing a radiation treatment plan involving a modulated scanning plan, the quality of the treatment is affected by, among other things, the minimum MU (min MU) for the treatment plan. Conventionally, in the context of IMPT planning optimization, for example, minimum MU is considered a system-wide parameter that dictates the minimum amount of dose a single spot is allowed to deliver. The minimum MU for the treatment plan is selected to suit the radiation therapy treatment system (also referred to as a delivery system) and treatment planning needs, wherein the minimum amount of radiation capable of being delivered by the delivery system (minimum allowable or minimum deliverable MU) dictates the lowest minimum MU that may be selected for the treatment plan. Beyond the minimum allowable MU constraint, the minimum MU may be chosen to balance the dosimetric quality of the treatment plan against the time each plan takes to deliver the treatment (treatment or delivery time).

The conventional system-wide (or global) minimum MU requires identification of a one-size-fits-all value that is deliverable at all beam energies and is a suitable trade-off between the delivery speed and target dose quality. However, with the selected minimum MU being a function of the beam energy, and a normal IMPT plan including multiple energy layers, any global minimum MU may not provide the optimal trade-off in all energy layers. That is, for example, there may be situations where, for an energy layer, a minimum MU different from the global minimum MU, may improve delivery time without sacrificing plan quality, or vice versa.

For example, a global minimum MU may lead to situations where an upper delivery speed limit of the delivery machine is exceeded at lower energy layers and/or the upper delivery speed limit is not reached at higher energy layers. This may result in lower plan quality without delivery time improvements and/or slower delivery times without plan quality improvements.

One or more example embodiments address at least the above-mentioned situations by utilizing a delivery machine parameter guided layer-wise minimum MU, rather than a global minimum MU. Machine parameters may also be referred to as machine limitations, machine parameter limitations, delivery limitations, physical delivery limitations or the like. In at least one example embodiment, a TPS may determine minimum MUs on a per-energy-layer basis, rather than globally. The minimum MUs may be based on machine parameters for the radiation therapy machine.

According to one or more example embodiments, machine limitations may be used as one of the boundary conditions for the MUs. However, example embodiments may also be applicable to instances in which the boundary conditions are set based on, for example, a user-preferred, user-defined or user-selected maximum/minimum MU.

Figure 5:
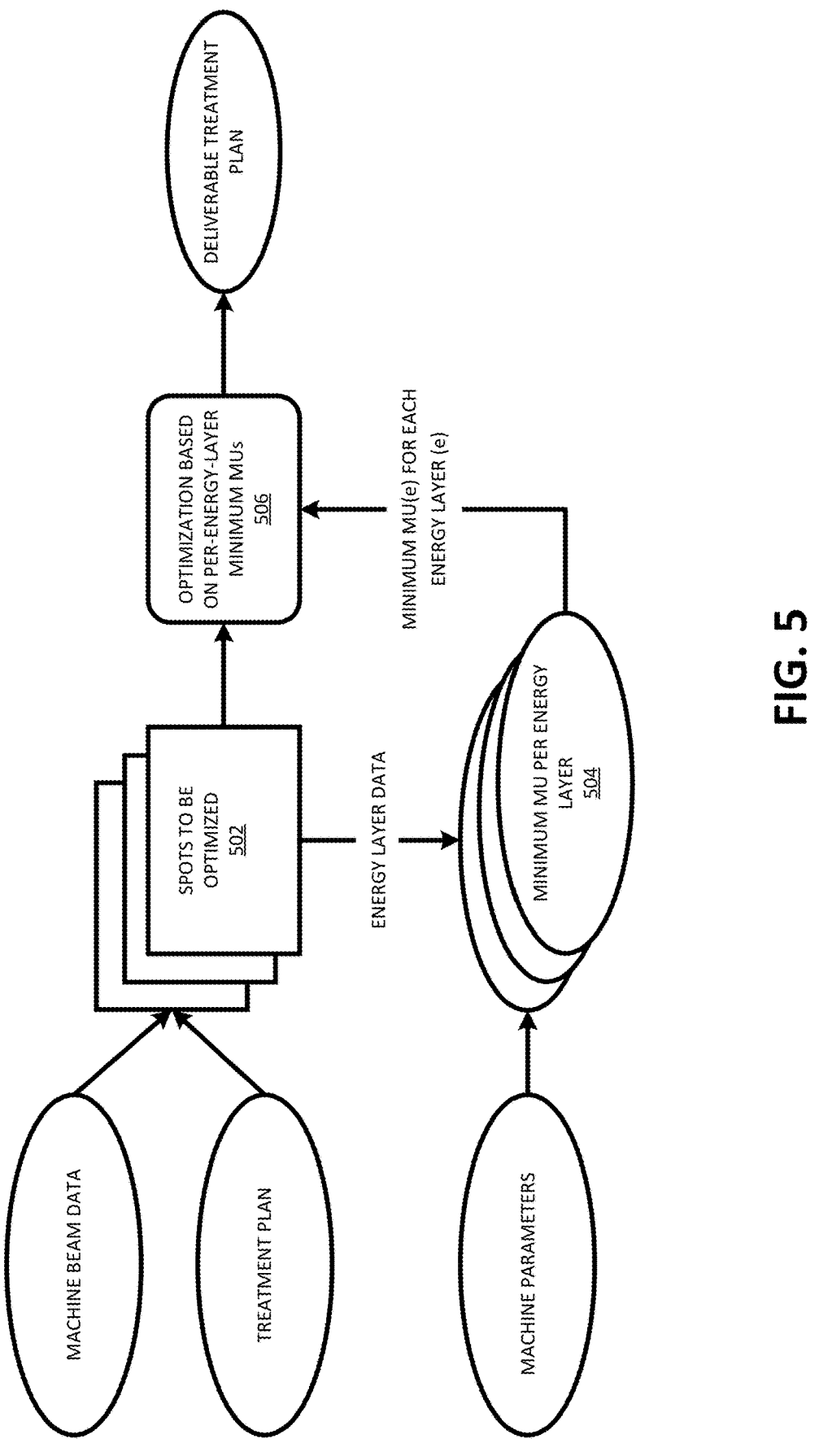
FIG. 5 is a functional block diagram illustrating a simplified example intensity modulated particle therapy (IMPT) optimization workflow, according to example embodiments.

FIG. 5 is a functional block diagram illustrating an example of a simplified IMPT optimization workflow, according to one or more example embodiments.

Conventionally, as discussed similarly above, machine beam data and treatment plan are used to generate the energy layers and spots within each energy layer for a treatment plan. The spot weights are subsequently optimized, and any spots with weights (MUs) below the global minimum MU (MUs between zero and the global minimum MU) are eliminated to generate a deliverable treatment plan.

As shown in FIG. 5, according to one or more example embodiments, the machine beam data and treatment plan are used to generate the energy layers and spots therein (502) and the spot weights are subsequently optimized (506). Rather than utilize a global minimum MU, however, the TPS 150 derives a minimum MU for each energy layer (504), which are used instead of the global minimum MU to eliminate any spots with weights or MUs below a minimum MU (MUs between zero and the minimum MU) for the respective energy layer to obtain a deliverable treatment plan.

Figure 6:
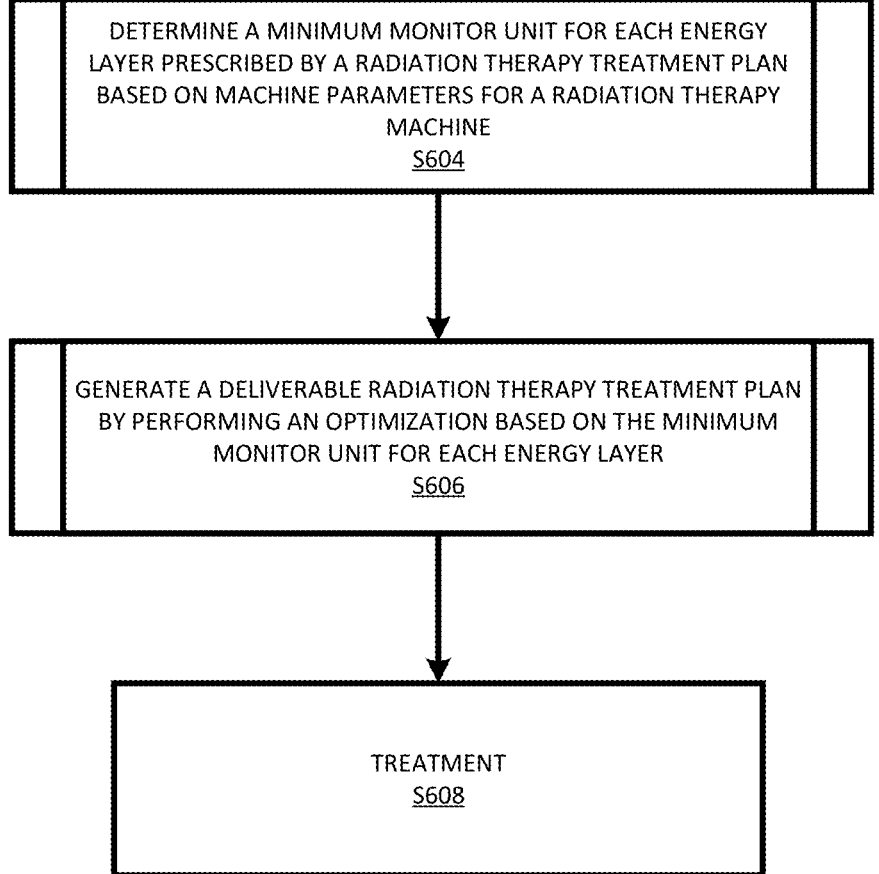
FIG. 6 is a flow chart illustrating a method for radiation therapy treatment planning and treatment, according to example embodiments.

FIG. 6 is a flow chart illustrating a method for radiation therapy treatment planning and treatment, according to example embodiments. The method shown in FIG. 6 will be discussed as being performed by the system shown in FIG. 1. Example embodiments should not, however, be limited to this example.

In accordance with the method of FIG. 6, the system shown in FIG. 1 (e.g., the TPS 150) may generate a radiation therapy treatment plan based on a plurality of minimum monitor unit values, wherein each of the plurality of minimum monitor unit values is for a respective energy layer among a plurality of energy layers prescribed by the radiation therapy treatment plan, and wherein each of the plurality of minimum monitor unit values is based on machine parameters (or machine limitations) for the radiation therapy machine 1000. The plurality of energy layers may be associated with a plurality of spots in a treatment target.

Referring more specifically to FIG. 6, at S604 the TPS 150 determines a minimum MU for each energy layer prescribed by a radiation therapy treatment plan based on machine parameters for the radiation therapy machine 1000 that is to deliver the radiation therapy treatment. In one example, the radiation therapy treatment plan may prescribe a plurality of energy layers associated with a plurality of spots in a treatment target, and the TPS 150 may determine a minimum MU for each of the plurality of energy layers based on machine parameters for the radiation therapy machine 1000. The minimum MU for each respective energy layer may be the same or different from minimum MUs for other energy layers; that is, one or more of the minimum MUs for the plurality of energy layers may be different from other minimum MUs for other ones of the plurality of energy layers. Example embodiments of methods for determining a minimum MU for a respective energy layer will be discussed in more detail later with regard to FIG. 7.

The TPS 150 may generate the radiation therapy treatment plan, for example, as discussed above with regard to FIGS. 3 and 4. Alternatively, the TPS 150 may obtain a previously generated radiation therapy treatment plan stored in, for example, memory 108 and/or 120.

Once having determined the minimum MU value for each energy layer, at S606 the TPS 150 generates a deliverable radiation therapy treatment plan by performing an optimization based on the minimum MU for each of the plurality of energy layers. Example embodiments of methods for determining a deliverable radiation therapy treatment plan will be discussed in more detail later with regard to FIG. 8.

Once determined, the deliverable radiation therapy treatment plan is output by the TPS 150 for use in treatment of the patient (e.g., via the radiation therapy machine 1000) at S608. Step S608 in FIG. 6 is the same as step 308 in FIG. 3, and thus, a detailed description will not be repeated here.

Figure 7:
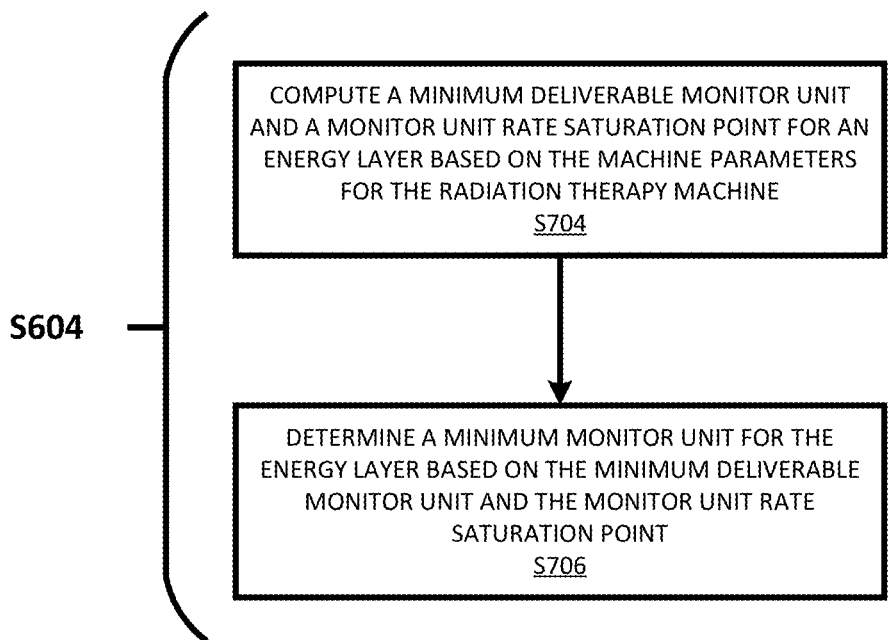
FIG. 7 is a flow chart illustrating an example embodiment of a method for determining a minimum monitory unit (MU) for an energy layer, according to example embodiments.

FIG. 7 is a flow chart illustrating an example embodiment of a method for determining a minimum MU for an energy layer at S604 in FIG. 6. The method shown in FIG. 7 will be discussed as being performed by the computer system 100 in FIG. 1, and more specifically the TPS 150, during plan development/evaluation/optimization 304. Example embodiments should not, however, be limited to this example. Although not illustrated, the method shown in FIG. 7 may be performed (e.g., iteratively, serially or in parallel) for each of the plurality of energy layers prescribed by the radiation therapy treatment plan. For the sake of brevity, however, only a single iteration in which a minimum MU is determined for an $e^{th}$ energy layer among the plurality of energy layers prescribed by the radiation therapy treatment plan, will be described in detail. In at least this example, the radiation therapy treatment plan may prescribe N energy layers and index e may take values from 1 to N.

Referring to FIG. 7, at S704 the TPS 150 computes a minimum deliverable MU (also referred to as the deliverability limit) min_del_MU and a MU rate saturation point MU_Rate_Sat_e for the $e^{th}$ energy layer based on the machine parameters for the radiation therapy machine. The MU rate saturation point may also be referred to as the MU saturation point. The minimum deliverable MU and the MU rate saturation point may be correlated to (e.g., a direct result of) the physical limitations of the delivery machine in performing radiation therapy treatment. As a result, the minimum deliverable MU and the MU rate saturation point may vary (e.g., slightly) from machine to machine.

According to at least one example embodiment, the machine parameters may include one or more of a MU rate range for the radiation therapy machine, a minimum spot duration for the radiation therapy machine, or transmission parameters for the radiation therapy machine. The MU rate range may define the minimum and maximum number of protons per second capable of being produced by the delivery machine. The MU rate range may be set for each energy layer prescribed by the radiation therapy treatment plan depending on the minimum MU of the energy layer. The MU rate range may be expressed in MUs per second (MU/s).

The minimum spot duration is the minimum beam duration (in seconds) capable of being emitted by the delivery machine. In practice, the beam duration is limited by the speed at which the hardware can reliably turn the beam off after having been turned on, and the accuracy at which the system can determine the number of emitted MUs during the beam delivery. For example, a system may require a few milliseconds for the hardware to turn off the beam after having been turned on. In another example, the measurement accuracy of emitted monitor units for the system may be limited to 0.1 MU and the MU rate may be 10 MU/s, which would result in the shortest amount of time that the beam can be on so that the emitted MUs are counted being 10 ms.

Transmission parameters for the radiation therapy machine include, for example, a coefficient of transmission, which represents the fraction of protons from the accelerator that reach the patient. Transmission parameters depend on beam energy, and thus, the transmission parameters may be lower for lower beam energies. The transmission parameters for a radiation therapy machine may be known a priori.

The lowest deliverable MU min_del_MU is the minimum amount of radiation that the radiation therapy machine can physically produce at once. In one example, the minimum deliverable MU min_del_MU is product of the minimum transmitted MU rate Tx_MU_Rate_min in MU/s and the minimum spot duration t_min_spot in, for example, milliseconds (min_del_MU=Tx_MU_Rate_min*t_min_spot). The minimum transmitted MU rate Tx_MU_Rate_min_e for an energy layer is the product of the transmission coefficient for the energy layer Transmission_e and the minimum MU rate MU_Rate_min for the delivery machine; that is, Tx_MU_Rate_min_e=Transmission_e*MU_Rate_min. The minimum transmitted MU rate Tx_MU_Rate_min for the delivery machine is the minimum transmitted MU rate Tx_MU_Rate_min_e from among the minimum transmitted MU rates for the plurality of energy layers. A delivery machine cannot deliver spots with a MU lower than the lowest deliverable MU, since doing so would require a MU rate and spot duration below the minimum thresholds for these values. Spots with higher MUs may be delivered using the same MU rate by extending the spot duration (how long the beam is on at that spot).

The MU rate saturation point is the MU value at which the delivery speed at the given energy layer no longer improves. The MU rate saturation point MU_Rate_Sat_e for an energy layer is reached when the minimum MU min_MU_e of the energy layer is equal to the product of the maximum transmitted MU rate Tx_MU_Rate_max_e for the energy layer and the minimum spot duration (min_MU_e=MU_Rate_Sat_e=Tx_MU_Rate_max_e*t_min_spot). As before, spots with higher MUs may be delivered by increasing the duration of irradiation.

As an example, if the MU rate range for the $e^{th}$ energy layer is [100, 6000] MU/s (i.e., a minimum MU rate of 100 MU/s and a maximum MU rate of 6000 MU/s), the minimum spot duration is 2 ms (t_min_spot=2 ms), and the transmission coefficient for the $e^{th}$ energy layer is 0.5, then the minimum deliverable MU min_del_MU for the $e^{th}$ energy layer would be min_del_MU_e=100 MU/s*0.002 s*0.5=0.1 MU. The MU rate saturation point for the $e^{th}$ energy layer MU_Rate_Sat_e would be MU_Rate_Sat_e=6000 MU/s*0.002 s*0.5=6 MU.

In at least some example embodiments, each energy layer may have a different transmission coefficient and MU rate range, and as a result, a different minimum deliverable MU and MU rate saturation point.

Still referring to FIG. 7, once having computed the minimum deliverable MU and the MU saturation point for the $e^{th}$ energy layer, at S706 the TPS 150 determines the minimum MU min_MU_e for the $e^{th}$ energy layer based on the minimum deliverable MU min_del_MU_e and/or the MU rate saturation point MU_Rate_Sat_e.

In one example, the TPS 150 sets the minimum MU for the $e^{th}$ energy layer to the MU rate saturation point for the $e^{th}$ energy layer (min_MU_e=MU_Rate_Sat_e). The MU rate saturation point may be calculated/computed by the TPS 150 during planning as discussed above. In another example, the TPS 150 may set the minimum MU to the MU rate saturation point for the energy layer, wherein the MU rate saturation point is obtained from a saturation curve for the delivery machine or selected from a lookup table. In the case of a saturation curve and/or lookup table, the saturation curve and/or the stored values may be determined, for example, in advance (e.g., prior to optimization) or during optimization.

In yet another example, the TPS 150 may select a value between the minimum deliverable MU min_del_MU_e and the MU rate saturation point MU_Rate_Sat_e as the minimum MU for the $e^{th}$ energy layer (min_del_MU_e<min_MU_e<MU_Rate_Sat_e).

In this case, the minimum MU may be selected by considering dose distribution, plan quality, etc. For example, if the minimum deliverable MU is considered '0%' and the MU rate saturation point is considered as '100%', setting the minimum MU to the MU rate saturation point for an energy layer may provide '100%' or a maximum delivery speed, while not exceeding the saturation limit. In some cases, however, radiation treatment plan utilizing a maximum delivery speed ('100%) does not provide an acceptable dose distribution, and as a result, some delivery speed must be exchanged to improve plan quality. In this case, the TPS 150 may select, for example, a minimum MU of 75% or other percentage of the MU rate saturation value depending on the dose distribution and/or other factors impacting plan quality.

Figure 10:
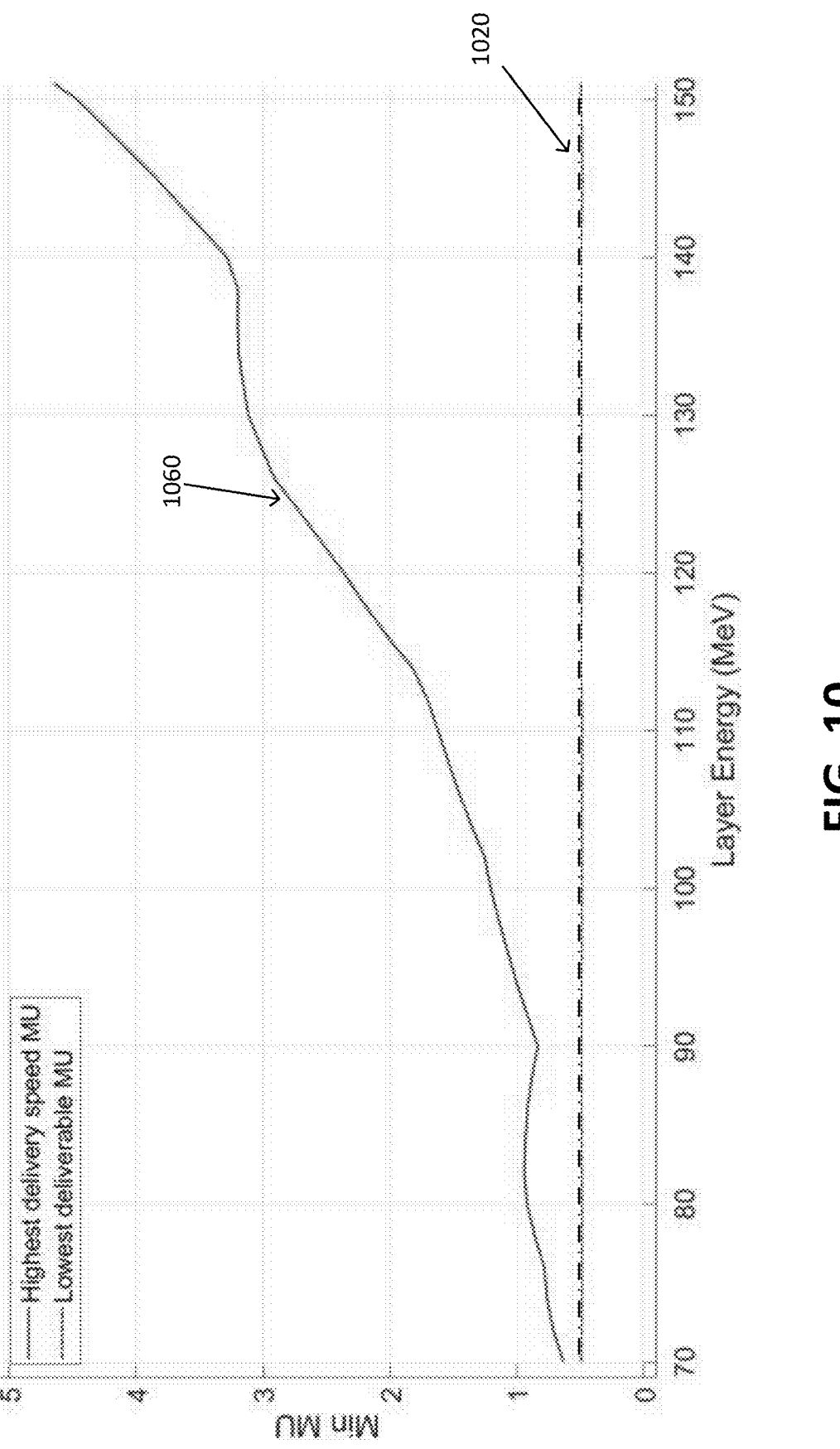
FIG. 10 is a graph illustrating an example saturation curve and a minimum deliverable MU for a delivery machine, according to example embodiments.

FIG. 10 is a graph illustrating an example saturation curve and a minimum deliverable MU for a delivery machine, according to example embodiments. In FIG. 10, the y-axis represents the minimum MU and the x-axis represents layer energy in MeV. As shown, limiting factors for the minimum MU of a treatment plan are the minimum deliverable MU 1020 (about 0.5 in FIG. 10) and the saturation point of MU rate for a given energy layer on the curve 1060. By setting minimum MUs for energy layers to values on the saturation curve, the delivery speed for a given energy layer (or radiation treatment) may be increased and/or maximized, and as a result, treatment time reduced and/or minimized.

Figure 8:
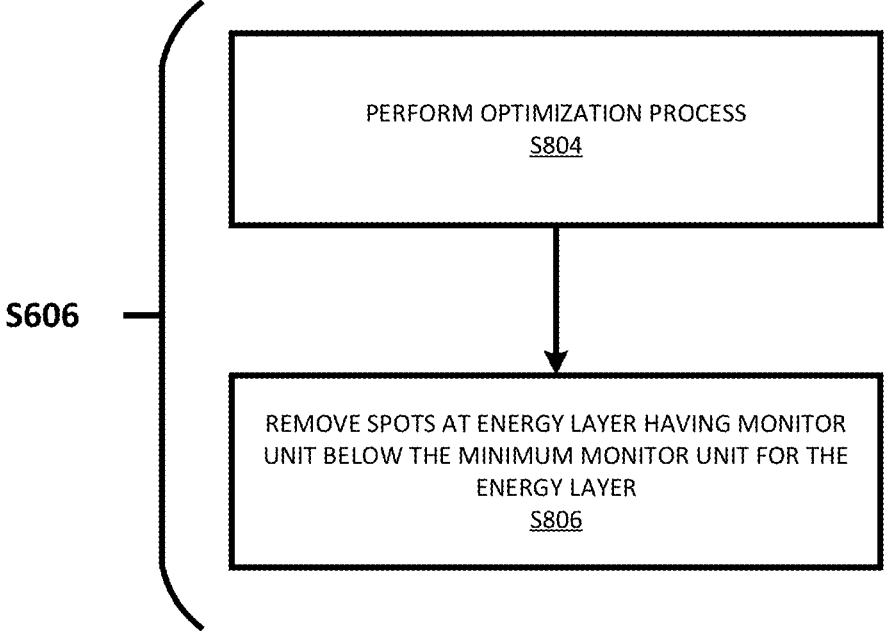
FIG. 8 is a flow chart illustrating an example embodiment of a method for generating a deliverable radiation plan, according to example embodiments.

FIG. 8 is a flow chart illustrating an example embodiment of a method for generating a deliverable radiation plan at S606 in FIG. 6. The method shown in FIG. 8 will be discussed as being performed by the computer system 100 in FIG. 1, and more specifically the TPS 150, during plan development/evaluation/optimization 304. Example embodiments should not, however, be limited to this example.

Referring to FIG. 8, at S804 the TPS 150 performs an optimization process as discussed above with regard to FIG. 4 to obtain a radiation treatment plan. In one example, the optimization process at S804 may be performed in any known manner. In another example, the TPS 150 may take into account the minimum MUs for each energy during optimization. In this example, the optimization process may be similar to those known in the art, but instead of taking into account a single global minimum MU as in the conventional art (e.g., using a constraint in the optimization such as that described in "Incorporating deliverable monitor unit constraints into spot intensity optimization in intensity-modulated proton therapy treatment planning," by Wenhua Cao et al. 2013 Phys. Med. Biol. 58 5113, the entire contents of which is incorporated herein by reference, or an additional term in the objective function), the optimization process may take into account the separate minimum MU value for each energy layer. In one example, the separate minimum MU values for each energy layer may be obtained and/or determined as discussed herein with regard to FIG. 7.

Because optimization processes taking into account a single global minimum MU are generally known, a further detailed discussion is omitted.

At S806, for each energy layer, the TPS 150 removes and/or eliminates all spots having MUs below the minimum MU for the energy layer to obtain a deliverable radiation therapy treatment plan. That is, for example, for each energy layer e from among the prescribed N energy layers of the radiation treatment plan, the TPS 150 removes all spots having MUs below the minimum MU min_MU_e for the energy layer e.

In at least one other example embodiment, the TPS 150 may determine the minimum MU per energy layer based on a minimum MU objective function $F_{MU}$, derived from the above-mentioned machine parameters (machine limitations), which may guide the optimization result towards higher minimum MUs per energy layer. For example, the TPS 150 may determine (e.g., during or prior to optimization) the minimum MU objective function $F_{MU}$ as a sum of energy layer-wise (per-energy-layer) and spot-wise (per-spot) cost functions $F_{MU}(e,j)$ that are piecewise linear as shown below.

$$F_{MU}(e, j) = 0, \text{ when } MU(j) \le \text{Deliverability Limit}(e)$$

$$= \frac{MU(j)}{\text{Saturation Limit}(e)}, \text{ when } MU(j) \le \text{Saturation Limit}(e)$$

$$= 1, \text{ when } MU(j) > \text{Saturation Limit}(e)$$

In the above example, MU(j) is the MU of j-th spot in the energy layer e, and the deliverability limit (minimum deliverable MU) and saturation limit (MU rate saturation point) are calculated for each energy layer from the machine parameters, for example, as discussed above with regard to FIG. 7. From minimum MU objective function $F_{MU}$ shown above, it can be seen that the minimum MU objective function $F_{MU}$ reaches a maximum at the MU rate saturation limit.

As exemplified below in Equation (1), for example, if the cost of the dosimetric objectives for a radiation therapy treatment plan is defined by objective function $F_D$, then the total cost function $F_{Tot}$ for optimization of the radiation therapy treatment plan may be based on the objective function $F_D$, a minimum MU objective function $F_{MU}$ and a weighting factor w balancing the objective function $F_D$ and the minimum MU objective function $F_{MU}$. In one example, the function $F_D$ may be similar to or the same as the dose objective function f(d) discussed above.

$$F_{Tot} = F_D w * F_{MU} \tag{1}$$

By maximizing the minimum MU objective function $F_{MU}$, the total cost function $F_{Tot}$ may be reduced and/or minimized.

By aiming to minimize the total cost function $F_{Tot}$, the weighting factor w controls the trade-off between dosimetric and minimum MU objectives, wherein w=0 yields a result that is only optimal regarding the dosimetric objectives (defined by function $F_D$) and w>>1 yields a result that substantially ignores the dosimetric objectives function $F_D$. By varying weighting factor w, the TPS 150 may obtain a suitable (or optimal) balance between the energy layer-wise minimum Mus and the dosimetric quality of the radiation treatment plan.

Figure 9:
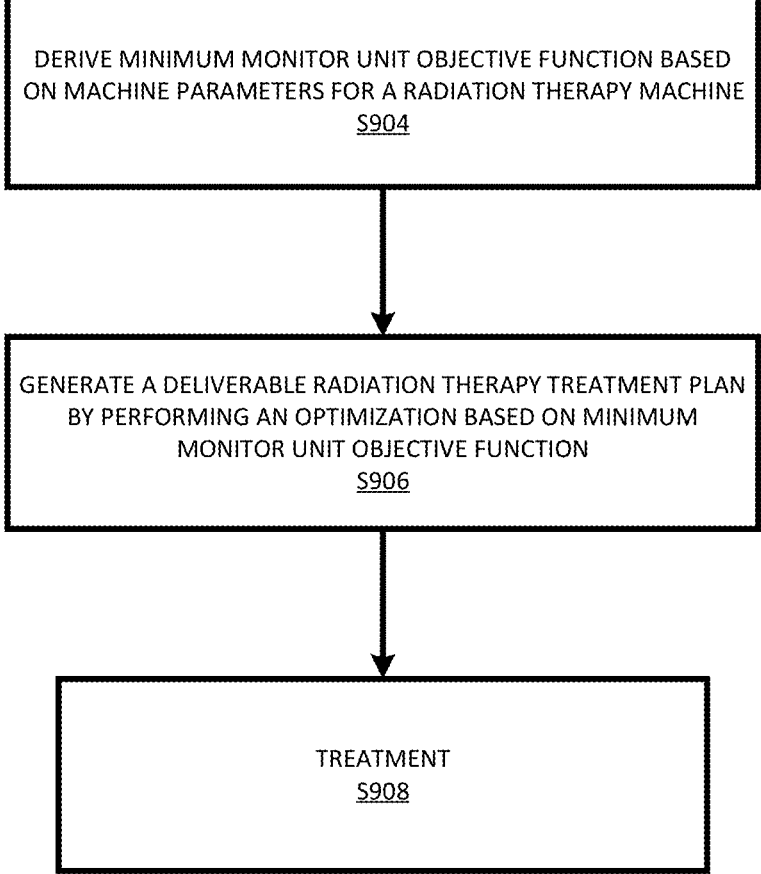
FIG. 9 is a flow chart illustrating another method for radiation therapy treatment planning and treatment, according to example embodiments.

FIG. 9 is a flow chart illustrating a method for radiation therapy treatment planning and treatment utilizing a minimum MU objective function, according to example embodiments. As with FIGS. 6-8, the method shown in FIG. 9 will be discussed as being performed by the system shown in FIG. 1. Example embodiments should not, however, be limited to this example.

In accordance with the method of FIG. 9, the TPS 150 may generate a radiation therapy treatment plan prescribing a plurality of energy layers associated with a plurality of spots in a treatment target, the radiation therapy treatment plan having a plurality of minimum MUs (minimum monitor unit values), wherein the plurality of minimum MUs are generated based on a minimum MU objective function for the radiation therapy machine 1000.

Referring more specifically to FIG. 9, at S904 the TPS 150 derives a minimum MU objective function $F_{MU}$ based on machine parameters (or limitations) for the radiation therapy machine 1000 that is to deliver the radiation therapy treatment. In one example, the TPS 150 may derive the minimum MU objective function $F_{MU}$ as a sum of layer-wise and spot-wise cost functions $F_{MU}(e,j)$ that are piecewise linear as discussed above.

At S906, the TPS 150 generates a deliverable radiation therapy treatment plan by performing an optimization based on at least the dosimetric objective function $F_D$, the minimum MU objective function $F_{MU}$ and a weighting factor w balancing the dosimetric objective function $F_D$ and the minimum MU objective function $F_{MU}$, as discussed earlier.

Once determined, the deliverable radiation therapy treatment plan is output by the TPS 150 for use in treatment of the patient (e.g., via the radiation therapy machine 1000) at S908. Step S908 in FIG. 9 is the same as step 308 in FIG. 3 and step S608 in FIG. 6, and thus, a detailed description will not be repeated here.

By utilizing an energy layer-wise minimum MU based on machine limitations of the radiation therapy machine, according to one or more example embodiments, field delivery times may be improved significantly (e.g., about 5 seconds or more in actual scanning time per field) with little to no effect on dose quality.

The following is a list of non-limiting illustrative embodiments disclosed herein.

Illustrative embodiment 1. A system for planning a radiation therapy treatment to be performed by a radiation therapy machine, the system comprising: a memory storing computer executable instructions; and at least one processor configured to execute the computer executable instructions to cause the system to generate a radiation therapy treatment plan prescribing a plurality of energy layers associated with a plurality of spots in a treatment target, the radiation therapy treatment plan being based on a plurality of minimum monitor unit values, each of the plurality of minimum monitor unit values being for a respective energy layer among the plurality of energy layers, and each of the plurality of minimum monitor unit values being based on machine parameters for the radiation therapy machine.

Illustrative embodiment 2. The system of illustrative embodiment 1, wherein the machine parameters include at least one of a monitor unit rate range for the radiation therapy machine, a minimum spot duration for the radiation therapy machine, or transmission parameters for the radiation therapy machine.

Illustrative embodiment 3. The system of any of the preceding illustrative embodiments, wherein the at least one processor is configured to execute the computer executable instructions to cause the system to: compute a minimum deliverable monitor unit value for a first energy layer, among the plurality of energy layers, based on the machine parameters for the radiation therapy machine, compute a monitor unit rate saturation point for the first energy layer based on the machine parameters for the radiation therapy machine, and determine a minimum monitor unit value for the first energy layer based on the minimum deliverable monitor unit value and the monitor unit rate saturation point for the first energy layer.

Illustrative embodiment 4. The system of any of the preceding illustrative embodiments, wherein the at least one processor is configured to execute the computer executable instructions to cause the system to determine the plurality of minimum monitor unit values based on a minimum monitor unit saturation curve for the radiation therapy machine, the minimum monitor unit saturation curve derived based on the machine parameters for the radiation therapy machine.

Illustrative embodiment 5. The system of any of the preceding illustrative embodiments, wherein the minimum monitor unit saturation curve is indicative of a minimum deliverable monitor unit value and a monitor unit rate saturation point for each of the plurality of energy layers.

Illustrative embodiment 6. The system of any of the preceding illustrative embodiments, wherein the minimum deliverable monitor unit value and the monitor unit rate saturation point for each of the plurality of energy layers are based on the machine parameters for the radiation therapy machine.

Illustrative embodiment 7. A radiation therapy treatment system, comprising: the system for planning a radiation therapy treatment according to any of the preceding illustrative embodiments; and the radiation therapy machine configured to provide radiation therapy treatment according to the radiation therapy treatment plan.

Illustrative embodiment 8. A system for planning a radiation therapy treatment to be performed by a radiation therapy machine, the system comprising: a memory storing computer executable instructions; and at least one processor configured to execute the computer executable instructions to cause the system to generate a radiation therapy treatment plan prescribing a plurality of energy layers associated with a plurality of spots in a treatment target, the radiation therapy treatment plan having a plurality of minimum monitor unit values, the plurality of minimum monitor unit values generated based on a minimum monitor unit objective function for the radiation therapy machine.

Illustrative embodiment 9. The system of illustrative embodiment 8, wherein the at least one processor is configured to execute the computer executable instructions to cause the system to derive the minimum monitor unit objective function based on machine parameters for the radiation therapy machine.

Illustrative embodiment 10. The system of any of illustrative embodiments 8-9, wherein the machine parameters include at least one of a monitor unit rate range for the radiation therapy machine, a minimum spot duration for the radiation therapy machine, or transmission parameters for the radiation therapy machine.

Illustrative embodiment 11. The system of any of illustrative embodiments 8-10, wherein each of the plurality of minimum monitor unit values is associated with a respective energy layer among the plurality of energy layers.

Illustrative embodiment 12. The system of any of illustrative embodiments 8-11, wherein the at least one processor is configured to execute the computer executable instructions to cause the system to generate the radiation therapy treatment plan according to at least the minimum monitor unit objective function, a dosimetric objective function and a weight factor.

Illustrative embodiment 13. The system of any of illustrative embodiments 8-12, wherein the minimum monitor unit objective function is a sum of energy layer and spot-wise cost functions that are piecewise linear.

Illustrative embodiment 14. A radiation therapy treatment system, comprising: the system for planning a radiation therapy treatment according to any of illustrative embodiments 8-13; and the radiation therapy machine configured to provide radiation therapy treatment according to the radiation therapy treatment plan.

Illustrative embodiment 15. A system for planning a radiation therapy treatment to be performed by a radiation therapy machine, the system comprising: a memory storing computer executable instructions; and at least one processor configured to execute the computer executable instructions to cause the system to generate a radiation therapy treatment plan for a treatment target based on a minimum monitor unit value for each of a plurality of energy layers prescribed by the radiation therapy treatment plan, each minimum monitor unit value based on machine parameters for the radiation therapy machine.

Illustrative embodiment 16. The system of illustrative embodiment 15, wherein the at least one processor is configured to execute the computer executable instructions to cause the system to generate the radiation therapy treatment plan by performing an optimization based on the minimum monitor unit value for each of the plurality of energy layers.

Illustrative embodiment 17. The system of any of illustrative embodiments 15-16, wherein the machine parameters include at least one of a monitor unit rate range for the radiation therapy machine, a minimum spot duration for the radiation therapy machine, or transmission parameters for the radiation therapy machine.

Illustrative embodiment 18. The system of any of illustrative embodiments 15-17, wherein the at least one processor is configured to execute the computer executable instructions to cause the system to compute a minimum deliverable monitor unit value for a first energy layer, among the plurality of energy layers, based on the machine parameters for the radiation therapy machine, compute a monitor unit rate saturation point for the first energy layer based on the machine parameters for the radiation therapy machine, and determine a minimum monitor unit value for the first energy layer based on the minimum deliverable monitor unit value and the monitor unit rate saturation point for the first energy layer.

Illustrative embodiment 19. The system of any of illustrative embodiments 15-18, wherein the at least one processor is configured to execute the computer executable instructions to cause the system to determine the minimum monitor unit value for each of the plurality of energy layers based on a minimum monitor unit saturation curve for the radiation therapy machine, the minimum monitor unit saturation curve derived based on the machine parameters for the radiation therapy machine.

Illustrative embodiment 20. A system for radiation therapy treatment, the system comprising: the system for planning a radiation therapy treatment according to any of illustrative embodiments 15-19; and the radiation therapy machine configured to apply radiation therapy treatment according to the radiation therapy treatment plan.

Although the terms first, second, etc. may be used herein to describe various elements, these elements should not be limited by these terms. These terms are only used to distinguish one element from another. For example, a first element could be termed a second element, and similarly, a second element could be termed a first element, without departing from the scope of this disclosure. As used herein, the term "and/or," includes any and all combinations of one or more of the associated listed items.

When an element is referred to as being "connected," or "coupled," to another element, it can be directly connected or coupled to the other element or intervening elements may be present. By contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Specific details are provided in the following description to provide a thorough understanding of example embodiments. However, it will be understood by one of ordinary skill in the art that example embodiments may be practiced without these specific details. For example, systems may be shown in block diagrams so as not to obscure the example embodiments in unnecessary detail. In other instances, well-known processes, structures and techniques may be shown without unnecessary detail in order to avoid obscuring example embodiments.

As discussed herein, illustrative embodiments will be described with reference to acts and symbolic representations of operations (e.g., in the form of flow charts, flow diagrams, data flow diagrams, structure diagrams, block diagrams, etc.) that may be implemented as program modules or functional processes include routines, programs, objects, components, data structures, etc., that perform particular tasks or implement particular abstract data types and may be implemented using existing hardware, for example, processing or control circuitry such as, but not limited to, one or more processors, one or more Central Processing Units (CPUs), one or more controllers, one or more arithmetic logic units (ALUs), one or more digital signal processors (DSPs), one or more microcomputers, one or more field programmable gate arrays (FPGAs), one or more System-on-Chips (SoCs), one or more programmable logic units (PLUS), one or more microprocessors, one or more Application Specific Integrated Circuits (ASICs), or any other device or devices capable of responding to and executing instructions in a defined manner.

Although a flow chart may describe the operations as a sequential process, many of the operations may be performed in parallel, concurrently or simultaneously. In addition, the order of the operations may be re-arranged. A process may be terminated when its operations are completed, but may also have additional steps not included in the figure. A process may correspond to a method, function, procedure, subroutine, subprogram, etc. When a process corresponds to a function, its termination may correspond to a return of the function to the calling function or the main function.

As disclosed herein, the term "memory," "storage medium," "processor readable medium," "computer read- able storage medium" or "non-transitory computer readable storage medium" may represent one or more devices for storing data, including read only memory (ROM), random access memory (RAM), magnetic RAM, core memory, magnetic disk storage mediums, optical storage mediums, flash memory devices and/or other tangible machine-read- able mediums for storing information. The term "computer- readable medium" may include, but is not limited to, por- table or fixed storage devices, optical storage devices, and various other mediums capable of storing, containing or carrying instruction(s) and/or data.

Furthermore, example embodiments may be implemented by hardware, software, firmware, middleware, microcode, hardware description languages, or any combination thereof. When implemented in software, firmware, middleware or microcode, the program code or code segments to perform the necessary tasks may be stored in a machine or computer readable medium such as a computer readable storage medium. When implemented in software, a processor or processors will perform the necessary tasks. For example, as mentioned above, according to one or more example embodiments, at least one memory may include or store computer program code, and the at least one memory and the computer program code may be configured to, with at least one processor, cause a network element or network device to perform the necessary tasks. Additionally, the processor, memory and example algorithms, encoded as computer program code, serve as means for providing or causing performance of operations discussed herein.

The terms "including" and/or "having," as used herein, are defined as comprising (i.e., open language). The term "coupled," as used herein, is defined as connected, although not necessarily directly, and not necessarily mechanically. Terminology derived from the word "indicating" (e.g., "indicates" and "indication") is intended to encompass all the various techniques available for communicating or ref- erencing the object/information being indicated. Some, but not all, examples of techniques available for communicating or referencing the object/information being indicated include the conveyance of the object/information being indicated, the conveyance of an identifier of the object/ information being indicated, the conveyance of information used to generate the object/information being indicated, the conveyance of some part or portion of the object/informa- tion being indicated, the conveyance of some derivation of the object/information being indicated, and the conveyance of some symbol representing the object/information being indicated.

According to example embodiments, medical systems, may be (or include) hardware, firmware, hardware executing software or any combination thereof. Such hardware may include processing or control circuitry such as, but not limited to, one or more processors, one or more CPUs, one or more controllers, one or more ALUs, one or more DSPs, one or more microcomputers, one or more FPGAs, one or more SoCs, one or more PLUS, one or more microproces- sors, one or more ASICs, or any other device or devices capable of responding to and executing instructions in a defined manner.

Benefits, other advantages, and solutions to problems have been described above with regard to specific embodi- ments. However, the benefits, advantages, solutions to problems, and any element(s) that may cause or result in such benefits, advantages, or solutions, or cause such benefits, advantages, or solutions to become more pronounced are not to be construed as a critical, required, or essential feature or element of any or all the claims.

What is claimed is:

1. A system for planning a radiation therapy treatment to be performed by a radiation therapy machine, the system comprising:

a memory storing computer executable instructions; and at least one processor configured to execute the computer executable instructions to cause the system to determine a plurality of minimum monitor unit values based on a minimum monitor unit saturation curve for the radiation therapy machine, the minimum monitor unit saturation curve derived based on machine parameters for the radiation therapy machine, and generate a radiation therapy treatment plan prescribing a plurality of energy layers associated with a plural- ity of spots in a treatment target, the radiation therapy treatment plan being based on the plurality of minimum monitor unit values, each of the plural- ity of minimum monitor unit values being for a respective energy layer among the plurality of energy layers, and each of the plurality of minimum monitor unit values being based on the machine parameters for the radiation therapy machine.

2. The system of claim 1, wherein the machine parameters include at least one of a monitor unit rate range for the radiation therapy machine, a minimum spot duration for the radiation therapy machine, or transmission parameters for the radiation therapy machine.

3. The system of claim 1, wherein the at least one processor is configured to execute the computer executable instructions to cause the system to compute a minimum deliverable monitor unit value for a first energy layer, among the plurality of energy layers, based on the machine parameters for the radiation therapy machine, compute a monitor unit rate saturation point for the first energy layer based on the machine parameters for the radiation therapy machine, and determine a minimum monitor unit value for the first energy layer based on the minimum deliverable moni- tor unit value and the monitor unit rate saturation point for the first energy layer.

4. The system of claim 1, wherein the minimum monitor unit saturation curve is indicative of a minimum deliverable monitor unit value and a monitor unit rate saturation point for each of the plurality of energy layers.

5. The system of claim 4, wherein the minimum deliver- able monitor unit value and the monitor unit rate saturation point for each of the plurality of energy layers are based on the machine parameters for the radiation therapy machine.

6. A radiation therapy treatment system, comprising:

the system for planning a radiation therapy treatment according to claim 1; and the radiation therapy machine configured to provide the radiation therapy treatment according to the radiation therapy treatment plan.

7. A system for planning a radiation therapy treatment to be performed by a radiation therapy machine, the system comprising:

a memory storing computer executable instructions; and at least one processor configured to execute the computer executable instructions to cause the system to generate a radiation therapy treatment plan prescribing a plurality of energy layers associated with a plurality of spots in a treatment target, the radiation therapy treatment plan having a plurality of minimum monitor unit values, the plurality of minimum monitor unit values generated based on a minimum monitor unit objective function for the radiation therapy machine, the minimum monitor unit objective function including a deliverability limit and a saturation limit for each energy layer of the plurality of energy layers.

8. The system of claim 7, wherein the at least one processor is configured to execute the computer executable instructions to cause the system to derive the minimum monitor unit objective function based on machine parameters for the radiation therapy machine.

9. The system of claim 8, wherein the machine parameters include at least one of a monitor unit rate range for the radiation therapy machine, a minimum spot duration for the radiation therapy machine, or transmission parameters for the radiation therapy machine.

10. The system of claim 7, wherein each of the plurality of minimum monitor unit values is associated with a respective energy layer among the plurality of energy layers.

11. The system of claim 7, wherein the at least one processor is configured to execute the computer executable instructions to cause the system to generate the radiation therapy treatment plan according to at least the minimum monitor unit objective function, a dosimetric objective function and a weight factor.

12. The system of claim 7, wherein the minimum monitor unit objective function is a sum of energy layer and spot-wise cost functions that are piecewise linear.

13. A radiation therapy treatment system, comprising:
the system for planning a radiation therapy treatment according to claim 7; and
the radiation therapy machine configured to provide the radiation therapy treatment according to the radiation therapy treatment plan.

14. A system for planning a radiation therapy treatment to be performed by a radiation therapy machine, the system comprising:
a memory storing computer executable instructions; and
at least one processor configured to execute the computer executable instructions to cause the system to
determine a minimum monitor unit value for each of a plurality of energy layers based on a minimum monitor unit saturation curve for the radiation therapy machine, the minimum monitor unit saturation curve derived based on machine parameters for the radiation therapy machine, and
generate a radiation therapy treatment plan for a treatment target based on the minimum monitor unit value for each of the plurality of energy layers prescribed by the radiation therapy treatment plan, each minimum monitor unit value based on the machine parameters for the radiation therapy machine.

15. The system of claim 14, wherein the at least one processor is configured to execute the computer executable instructions to cause the system to generate the radiation therapy treatment plan by performing an optimization based on the minimum monitor unit value for each of the plurality of energy layers.

16. The system of claim 14, wherein the machine parameters include at least one of a monitor unit rate range for the radiation therapy machine, a minimum spot duration for the radiation therapy machine, or transmission parameters for the radiation therapy machine.

17. The system of claim 14, wherein the at least one processor is configured to execute the computer executable instructions to cause the system to
compute a minimum deliverable monitor unit value for a first energy layer, among the plurality of energy layers, based on the machine parameters for the radiation therapy machine,
compute a monitor unit rate saturation point for the first energy layer based on the machine parameters for the radiation therapy machine, and
determine the minimum monitor unit value for the first energy layer based on the minimum deliverable monitor unit value and the monitor unit rate saturation point for the first energy layer.

18. A system for radiation therapy treatment, the system comprising:
the system for planning the radiation therapy treatment according to claim 14; and
the radiation therapy machine configured to apply the radiation therapy treatment according to the radiation therapy treatment plan.

* * * * *